United States Patent [19]
Boyde

[11] Patent Number: 5,882,318
[45] Date of Patent: Mar. 16, 1999

[54] MULTICHAMBER CONTAINER FOR BLOOD OR OTHER FLUID SAMPLES

[75] Inventor: Tom Robin Caine Boyde, London, England

[73] Assignee: Tom Robin Caine Boyde, London, England

[21] Appl. No.: 411,687

[22] PCT Filed: Sep. 28, 1993

[86] PCT No.: PCT/GB93/02018

§ 371 Date: Apr. 27, 1995

§ 102(e) Date: Apr. 27, 1995

[87] PCT Pub. No.: WO94/07415

PCT Pub. Date: Apr. 14, 1994

[30] Foreign Application Priority Data

Sep. 30, 1992 [GB] United Kingdom .................... 9220597

[51] Int. Cl.⁶ ....................................................... A61B 5/00
[52] U.S. Cl. ........................................................... 600/595
[58] Field of Search ..................................... 128/760, 762, 128/764; 604/403, 411–414; 600/573, 575–577

[56] References Cited

U.S. PATENT DOCUMENTS 3,382,865  5/1968  Worrall .
3,706,305  12/1972  Berger et al. .
4,194,509  3/1980  Pickering et al. .................. 128/350 R

FOREIGN PATENT DOCUMENTS 0448795  2/1991  European Pat. Off. .

*Primary Examiner*—Max Hindenburg
*Attorney, Agent, or Firm*—Banner & Witcoff Ltd

[57] ABSTRACT

A device for taking fluid samples, comprising sample chambers which are separable after filling, have self sealing closures and are so disposed that a needle can fill them successively without withdrawal from an initially pierced closure that separates the chambers, or the first of them from the exterior.

11 Claims, 3 Drawing Sheets

FIG.4a
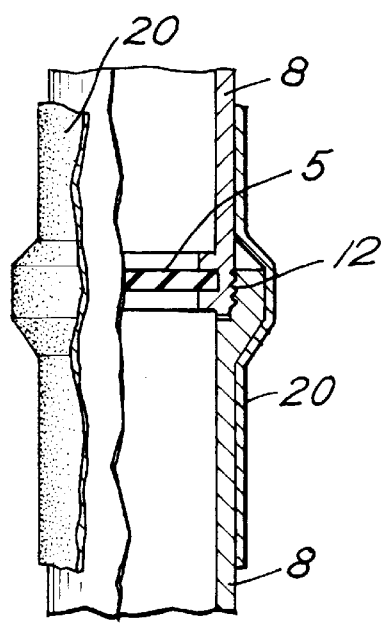
FIG.4b
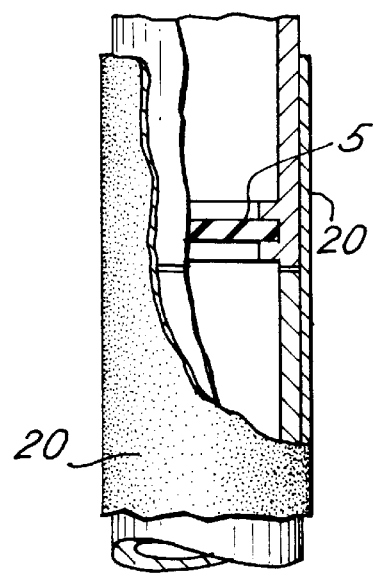
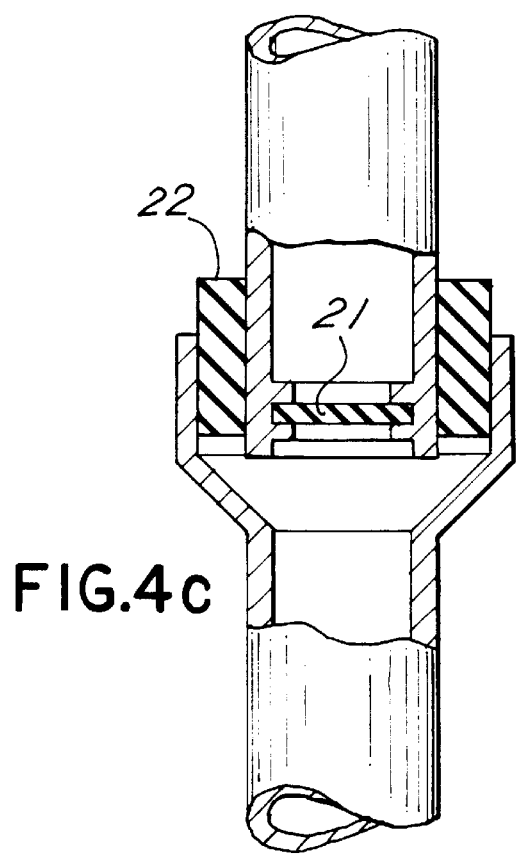
FIG.4c

MULTICHAMBER CONTAINER FOR BLOOD OR OTHER FLUID SAMPLES

This is a submission under 35 U.S.C. 371 of PCT GB93/02018.

AREA OF THE INVENTION

Much of what follows refers specifically to the collection of samples of venous or arterial blood for the performance of chemical, biochemical, biological or physical tests; as is often required in the practice of medicine for diagnosis of disease, control of treatment, or monitoring of progress. The principles of the invention are however applicable more widely, to the collection of other fluids whether or pathological or biological nature, or otherwise.

PROBLEMS

The procedures and equipment used at present for taking blood samples remain imperfect, with many problems. Those particularly addressed by the present invention are as follows:

i) It is frequently necessary to take several samples of blood from one patient at one time for different tests. To avoid undue distress to the patient from multiple skin punctures, but also because for some diagnostic and analytical purposes it is desirable that all the different samples are known to come from a single site at exactly the same time, blood is drawn from the blood vessel through a needle or an in-dwelling catheter and distributed between several pre-prepared containers, with or without the intervention of a syringe to serve as a primary but temporary extracorporeal receptacle. The eventual containers differ most often in respect of the additives placed within them to prevent coagulation (according to the test to be done), or to encourage coagulation, or to facilitate separation of cells from the fluid portion of blood, etc. But they may differ also in size, and even if containing the same additives, separate containers may be required for despatch to different analysts.

ii) In nearly every case the blood must be distributed immediately between eventual containers, adjacent to and within view of the patient. This is anyway a tense situation, made more so by the manipulative difficulties. Tension is communicated to the patient, with adverse effects which are greater because he (or she) is anyway concerned about losing even a little blood, is usually upset by the mere sight of blood, and more so if it is spilled.

iii) After any blood-sampling operation, traces of blood are inevitably found on the cotton swabs which are invariably used, or the outside of the container, needle or other apparatus. But in a multiple-sampling operation such spillage is much more extensive. Any such contact between the sampled blood and the environment is undesirable for two distance reasons—the blood itself may be altered so that the test result is incorrect or misleading, and there is a health hazard from blood contacting other people (e.g. AIDS infection of health-care personnel).

iv) The containers for blood for analysis must be labelled to show that they come from the patient concerned, and at what date and time. Whether or not a system of pre-labelling is used, the conditions of blood-taking are such that confusion of labelling is frequent. The laboratory or other personnel carrying out the tests have usually no direct means of detecting that an error has occurred, so that the result reported appears to refer to the patient and/or sampling time concerned but in fact is based on analysis of a sample from a quite different person or a different time. Commonly two samples are interchanged, so that results on two patients or two sampling times are affected. The consequences of this type of error can be serious, even fatal, and moreover, if the cause is not detected, there may be loss of confidence in test results for the future.

When an indwelling catheter is used, it must be filled with a solution to prevent coagulation, and in any case is commonly used for infusion of fluids. Thus, when a blood sample is to be drawn from an indwelling catheter, the first portion of fluid flowing from the catheter is not blood at all, or not a representative sample, and must not be used for analysis. To a lesser degree, the first portion of any sample of blood drawn via conventional venous or arterial puncture should be viewed as non-representative. Whether the matter is sufficiently serious to demand action varies according to the tests required.

A point of great importance in sampling blood is that a sampling needle should never be exposed to a non-evacuated space while it is in communication with the source of the sample. Samples are commonly of venous blood, where the pressure within the blood vessel can easily be negative relative to atmosphere (e.g. in a raised arm, as blood drains to the heart). A needle exposed to atmosphere in such circumstances can draw air, with disastrous consequences for the patient.

vii) Ease of manipulative procedure is of positive benefit to health as discussed under (ii) and (iii) above. But medical services must be delivered at low cost if they are to be available to the whole population. Also, equipment for taking or handling blood should preferably not be re-used, for reasons analogous to those under (iii). Thus sample containers should be constructed of such materials, and of such a simple design as to be inexpensive and disposable, as well as being easy in use.

PRIOR ART

The problems discussed above are well recognised, and numerous designs and patents exist which address one or more of them.

1a) Self-sealing stopper and hollow needle

A convenience of the use of a pre-evacuated or evacuable container with a self-sealing stopper of rubber or a similar material is that, when the stopper is penetrated by a needle, blood up to a predetermined volume can flow into the container without any further action by the operator other than to keep the channel for blood flow unobstructed. For a single sample of blood this can minimise spillage and patient distress. See e.g. what is possibly the first use of a self-sealing penetrable rubber stopper, Kleiner U.S. Pat. No. 2,460,641 ref. 15. A further reference that may be mentioned, though not concerned with blood sampling, is Chavarot Fr. 950 588 ref. 16.

b) Evacuated Container

Using a different means for sealing the evacuated container, the earliest patent is probably Brown U.S. Pat. No. 1,124,285 ref. 17, possibly the first pre-evacuated blood-taking vessel.

c) Allowing escape of gas

If non-evacuated containers with perforable seal are used (with needle) means must necessarily be provided for removing or allowing escape of the air or gas enclosed.

2) Means of controlling flow from a double-ended needle, or catheter, i.e. how to minimise blood spillage as several different containers are filled in turn Common practice at the present day, though not universal is to use a double-ended needle of which the extra-corporeal end is shrouded with a soft rubber sheath resembling a condom in geometry, though not in size. The sheath is penetrated easily when the extra-corporeal needle-end is thrust the rubber stopper of an evacuated sample tube, but up to that time has acted as a valve preventing premature escape of blood. When the needle is withdrawn, the sheath re-seals at least in part, and thus limits the spillage of blood as several different evacuated sample containers are attached in turn. Such means are only partly successful in preventing spillage of blood. Such needle-sheaths tackle problems (i) and (iii) in an inexpensive manner, but with only partial success—and running through a series of sample containers at the bedside cannot be called elegant. For illustrations (but not the original invention) see refs. 1–3.

Other additional on-off valve systems are described in many patents, of which examples are refs. 1, 2, 4–6.

Any on-off valve system should be helpful in limiting blood spillage, but these do not meet the requirement for simplicity (vii).

3) Simultaneous distribution of blood to several separate containers

Refs. 7–10 cover devices which attempt to solve problem (i) by allowing blood from a single venepuncture to flow along a system of channels to several containers in a manner which is, in principle totally enclosed. Thus blood spillage (iii) should be minimal, at least at the bedside—limited to the venepuncture itself. These devices are relatively complex and costly, and there are difficulties of scale and of maintaining flow.

Chamber intermediate between blood source and collection container

Many patents provide for a preliminary chamber between the extracorporeal needle-end and the main blood collection chamber, or a chamber within the double-ended needle system itself (e.g. refs. 5, 7, 11–13). The objective vary. The most consistently cited objective is a "tell-tale" to allow the operator to confirm that the venepuncture needle is in place by the appearance of blood in this "tell-tale chamber", for example Percarpio U.S. Pat. No. 4,155,350 ref. 13.

Here the stopper of an evacuated collection container is itself hollow—and made of translucent material so that its contents can be seen. Advantages cited are that the angle of the needle to the vein is variable and flexible, and blood can be seen to enter the hollow stopper, confirming that the venepuncture needle has reached its target and is within a blood-filled space. However there is no suggestion that the stopper is used to collect a sample; it is not for example evacuated and contains no materials such as anticoagulants.

McDonald U.S. Pat. No. 3,937,213 ref. 14 describes what is more a system or kit of units than a single device. Blood is collected from an intravenous needle and flexible tube into a first evacuated container. Then in a second operation, with or without prior centrifugation to separate cells from plasma or serum, blood or the liquid portion of blood is transferred (again via needles and flexible tubes) into a second evacuated chamber, within which are individual sample tubes which can be filled in turn or the sample tubes are each individually evacuated. There are many subsidiary features to the system. Although the system fulfils several of the intended functions of the present invention, the concept of filling chambers in turn by passing one needle successively through outer and one or more inner dividing closures is not present. There are objections too on the basis of complexity, fiddly operation, risk of contamination of laboratory personnel, mis-identification of samples, etc.

Worrall U.S. Pat. No. 3,382,865 applies two or more separate containers to a fixed needle but he does not appreciate the problems of contamination, or confusion of samples, nor that of exposure of the sampling needle to atmospheric pressure, as appears from the very fact that he shows successive containers applied to a fixed needle.

| | References | |
|---|---|---|
| 1. | Ritter | DE 3 740 269 |
| 2. | Wanderer | US 4 731 059 |
| 3. | Zanotti | US 5 084 034 |
| 4. | Russo | US 3 494 352 |
| 5. | Abramson | US 4 166 450 |
| 6. | Christinger | US 4 441 951 |
| 7. | Cinqualbre | US 3 405 706 |
| 8. | Horn | US 3 494 351 |
| 9. | Sausse | US 3 696 806 |
| 10. | Cinqualbre | US 3 848 581 |
| 11. | Kaufman | US 4 340 068 |
| 12. | Percarpio | US 4 886 072 |
| 13. | Percarpio | US 4 155 350 |
| 14. | McDonald | US 3 937 213 |
| 15. | Kleiner | US 2 460 641 |
| 16. | Shavarot | FR    950 588 |
| 17. | Brown | US 1 124 285 |
| 18. | Becton, Dickinson | AU    627 387 |
| 19. | Terumo K. K. | JP 62-51238 (63-216542) |
| 20. | Worrall | US 3 382 865 |

PRINCIPLES OF THE INVENTION

Important features of the invention are set out in the claims but are also discussed generally below.

Most broadly the invention lies in a container for taking samples of blood or other fluid, having tow or more sample chambers, so disposed that a hollow needle, in communication with a source of the fluid can fill them individually in succession for separate subsequent use, characterised in that the chambers have perforable, self sealing diaphragm or other closures and are so disposed and pre-evacuated, that filling can be conducted without withdrawal of the needle from an initially pierced closure that separates the chambers or the first of them from the exterior, and without exposure of the needle to a non-evacuated space while in communication with the source of the sample, and in that the chambers can be separated from each other after filling.

The device thus consists of a number of chambers for receiving blood or other fluid, which are separated from each other and from the environment by perforable, self-sealing diaphragms, stoppers or like closures. The chambers are so arranged that a hollow needle which is in communication with a source of blood or other fluid can be passed through an outer closure and then through one or more inner closures, each chamber being filled in turn. Most simply, the chambers and closures form a linear sequence so that the needle passes through each preceding chamber on its way to the next—filling them on advance or withdrawal. However where chambers are not linearly successive an outer diaphragm is pierced then, without withdrawal, the diaphragms of successive chambers below are pierced by relative movement of needle, chambers or both. The linearly successive chambers are simplest to provide and use. Chambers in parallel may however have advantages, particularly in provision of all chambers with a rounded end integral with the main body of the chamber and more resistant to centrifugation than designs in which lower end of the tube is closed with an elastomeric plug.

The connections between chambers, in the assembled device, are required to be gas-tight. For cheap disposable devices to be manufactured in plastics, or glass, suitable connection is for example by means of elastomeric plugs, or screw threads, or a sealing wrap, or by continuity of the matrix across the join. For separation, glass for example can readily be induced to crack along predetermined lines, as in ampoules of injection drugs, or a sealing wrap can be cut with a knife.

Generally, separation of the chambers after filling with sample can be by unscrewing, by disconnecting a joint relying on an elastomeric plug, or by cutting (whether through the matrix of the material which forms the chambers, a plug which forms the junction, or a sealing wrap), though there is no limitation to any particular method.

After filling, the chambers are separated from each other and the contents of each are available to be used for different purposes, despatched to different destinations, etc. Preferably, the chambers should be joined together in such a way that after separation from each other they cannot be re-united, or alternatively that it will be obvious upon inspection that such separation has previously occurred. This is automatic when to separate the chambers the closures are sliced through within their thickness, separating the chambers but leaving them sealed, but for example a sealing wrap also gives a tamper-evident assembly very conveniently.

During manufacture, arrangements are made to place within each chamber a suitable additive (or no additive) so that the blood or other fluid is suitably prepared for whatever purpose is intended. The chambers of one device may contain different additives or the same additive, and may differ in volume.

Preferably also, during manufacture, all the chambers of each device are marked in a permanent and preferably machine readable way to indicate that they belong to one set.

BRIEF DESCRIPTION OF THE DRAWING

In the detailed description that follows, reference may be made to the drawing comprised of the following figures:

FIG. 4A is a partial cross sectional view of a connection assembly for connecting adjacent chambers of the container of the invention;

FIG. 4B is an elevation view of another alternative connection assembly for connecting chambers or elements forming the container of the invention; and FIG. 4C is an elevation view of yet another embodiment of the connection between adjacent chambers or elements forming the container of the invention.

DETAILED DESCRIPTION

FIGS. 1–4, enlarged and not to scale in detail, illustrate alternative embodiments of the invention but these are not necessarily the only possibilities. Different aspects of the use of the invention are shown in the various figures, and it is to be understood that aspects not shown in a particular figure may be applicable to that embodiment.

Figure 1:
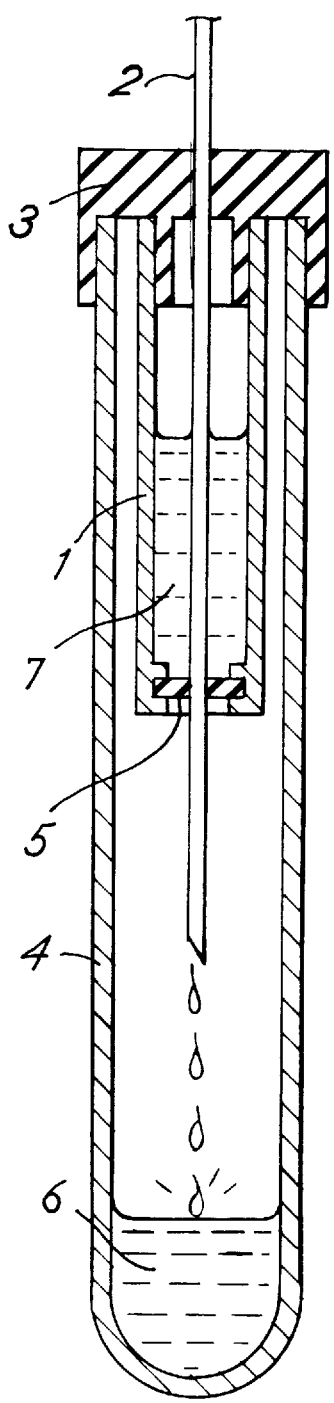
FIG. 1 is a cross sectional view of the first embodiment of the invention.

FIG. 1 shows an embodiment in which the first chamber (1) to be penetrated by the needle (2) is attached to or forms part of the stopper (3) of a larger sample container (4), and would be separated from that container by the act of removing the stopper (3). Only two chambers (or spaces) are shown, but additional spaces could be provided by way of a construction resembling that in FIG. 2 or otherwise. As drawn, the needle (2) is shown penetrating through the first chamber (1) and a self-sealing membrane (5) into the second chamber (4), into which it is delivering blood (6), having already partially filled the first chamber (7): both chambers had been fully or partially evacuated before use. The needle (2) shown either forms part of a double-ended needle system or is attached to a syringe or an indwelling catheter.

Figure 2A:
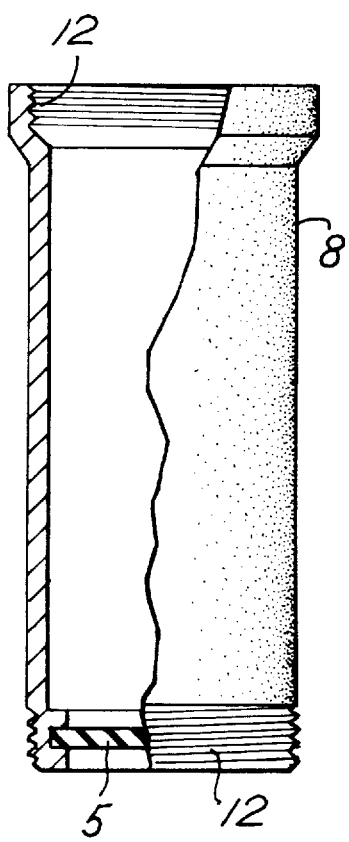
FIG. 2A is a partial cross sectional elevation depicting an element of a second embodiment of the invention.
Figure 2B:
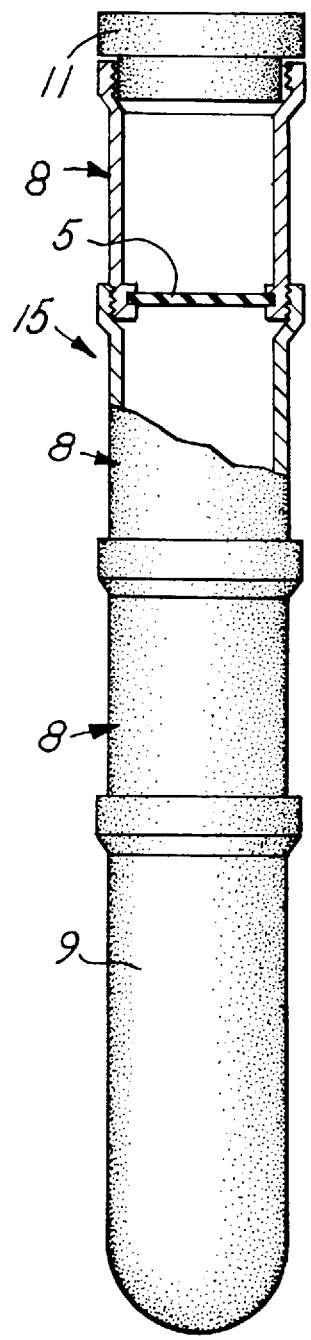
FIG. 2B comprises a partial cross sectional elevation of elements of FIG. 2A in combination to form the container of the invention.

FIGS. 2A and 2B show an embodiment in which a series of units (8) screw into each other to form a stack (15), which may in principle be of any number of units, and the individual units may differ in length. As drawn, the lower unit (9) has a rounded, closed end (10) so that it can be used as a centrifuge tube, usually but not necessarily after separating from the other units. As drawn, the upper unit is sealed at the top end by a stopper (11) of rubber-like material, but an empty unit or adapted (short) unit can also serve for this purpose. For use as a series of evacuated units, the screw fitting (12) must be so designed and made as to hold the vacuum, or for example a sealing wrap as discussed below used It is also possible to fuse the lower to the upper unit at one or more points around the circumference of each join such that the units concerned cannot be unscrewed and thus separated from each other without breaking the fused portions. As shown in FIG. 2A, if reassembled, it is then visible to inspection that the fused portion has already been broken and therefore that the units have been dis-assembled at some earlier time.

Figure 3A:
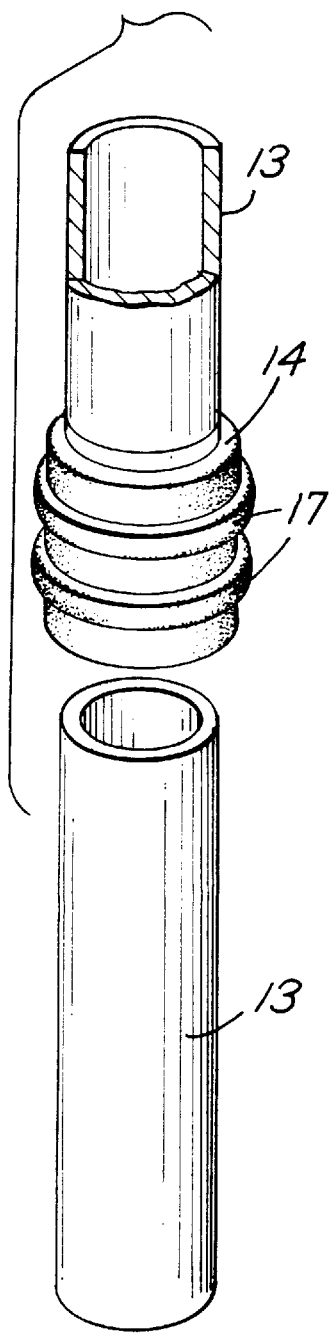
FIG. 3A is an isometric view of another embodiment of the invention.
Figure 3B:
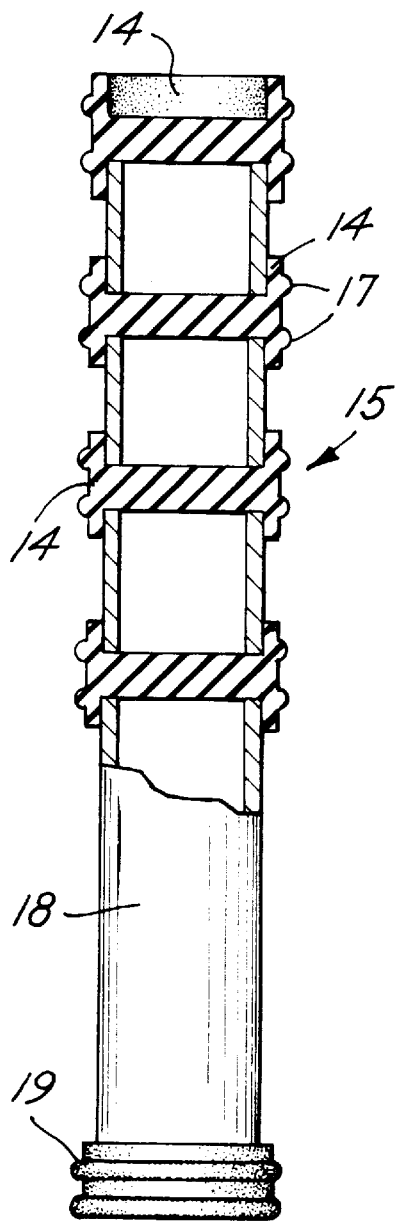
FIG. 3B is a cross sectional elevation depicting the container of FIG. 3A.
Figure 3C:
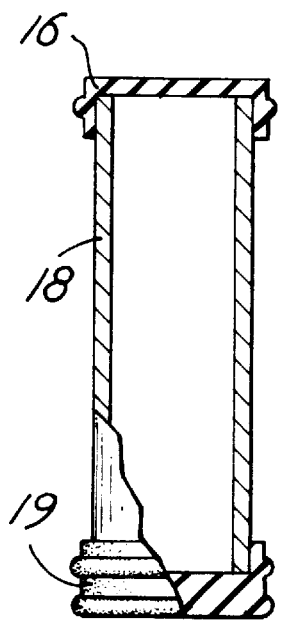
FIG. 3C is a cross sectional elevation of an element of the container of FIG. 3B.

FIG. 3A shows an embodiment in which the chambers each consist of a length of tubing (1) usually of clear or translucent rigid plastic, with open ends which are sealed and enclosed by a double-sided elastomeric plug (14). In this embodiment, the device consists of a stack (15) of such chambers which are divided from each other after filling by cutting through each of the intermediate elastomeric plugs (14) in such a way that the integrity as a plug is maintained on both sides of the cut (16), as shown in FIGS. 3B and 3C. As drawn, the plug has ridges (17) to define the point of cut, but this is not an essential features. As drawn, the lower chamber (18) is of larger volume than the others and is designed to be subjected to centrifugation using the lower elastomeric plug (19) as a base. Neither of these however is an essential feature. In particular, the lower chamber may be constructed with an integral, rounded, rigid, plastic base such as is illustrated in FIG. 2 (10), and this is preferred at higher centrifugal forces to obviate the risk of leakage.

The detailed additional drawings of FIG. 4 show an elastomeric wrap (20) that in FIG. 4*a* may be used with the screwed assembly of FIG. 2 or in FIG. 4*b* in an assembly where the wrap alone secures units in the series. Such wraps conveniently provide both sealing, and a tamper-evident construction, in that the wrap is destroyed on removal, or at least cut, to separate the units. FIG. 4*c* shows a further method of assembling units where a sealed-in pierceable membrane (21) like that in FIG. 2 is used but there is a separate elastomeric assembly plug (22) corresponding in that respect to the plugs (14) of the units of FIG. 3.

Method of Use

As to filling with blood or other liquid, the method of use in all these embodiments is the same.

If a syringe is used, it is first filled with blood and the needle (2) is then thrust down through the stopper (3) and blood allowed to run into the first chamber (1). When it is full, or sufficiently full, or pressures have equalised, the needle is thrust further through diaphragm (5) into the lower chamber (4), and this in turn is allowed to fill. The needle is then withdrawn and the chambers are separated, in the case of the embodiment of FIG. 1 by removing the stopper (3), open chambers are sealed, as may be required for some chambers in the embodiments of FIGS. 1 and 2, and the separated chambers despatched to their intended destinations.

alternatively, the needle may form part of a double-ended needle system. In that case, once the lower (most distant) chamber is appropriately filled, the intravenous needle will be first withdrawn from the vein (unless special circumstances dictate otherwise) before the extracorporeal needle-end is withdrawn from the device.

Alternatively, the needle may be attached to an indwelling catheter. In this case, the first chamber would be for discard, as discussed above, and would be appropriately sized to ensure that all contaminants from the lumen of the catheter were flushed out by fresh blood flowing from the blood-vessel. When all chambers were filled, the flow of blood from the catheter would be arrested by a valve or other means before withdrawing the needle from this device.

I claim:

1. A container for taking samples of blood or other fluid, having two or more sample chambers so disposed that a hollow needle, in communication with a source of the fluid can fill them individually in succession for separate subsequent use, characterized in that the chambers are pre-evacuated and have perforable, self sealing closures positioned in combination with each of said chambers, said closures including means whereby filling each separate chamber can be conducted without withdrawal of the needle from an initially pierced closure that separates the chambers or the first of them from the exterior, and without exposure of the needle to the exterior while in communication with the source of the sample and in that after filling the chambers by the needle, the needle can be withdrawn to the exterior and the chambers can be separated from each other.

2. A container according to claim 1 wherein the chambers are in a linear series separated by a corresponding series of closures successively pierced by the needle.

3. A container according to claim 2 wherein the chambers are separable by cutting the or each separating closure, still sealed, across within its thickness.

4. A container according to claim 1 wherein the chambers are united by a sealing wrap or other tamper-evident means.

5. A method of taking samples of blood or other fluid wherein the chambers of a container as claimed in claim 1 are filled with samples by use of the hollow needle, and are separated for subsequent analysis or test of the samples.

6. A container for taking samples of blood or other fluid comprising, in combination:

an array of linear, successive sample chambers defining a unitary container, each of said chambers separated from an adjacent chamber by a single, self-sealing diaphragm, said unitary container comprised of a rigid material forming the side walls of each chamber and said diaphragm forming at least one end wall of each chamber, said diaphragms axially aligned with one another for receipt of a hollow needle piercing therethrough sequentially upon advance or withdrawal of said needle into the chambers, said chamber side walls being connected together to form the unitary container by a releasable connection element joining the side walls together, said needle connectable to each of said chambers without intervening exposure thereof to the exterior of the container.

7. The container of claim 6 wherein the connection element comprises a threaded connection of the side walls.

8. The container of claim 6 wherein the connection element comprises a single sealing member capable of being severed to thereby separate adjacent chambers.

9. The container of claim 6 wherein the connection element includes a wrap seal joining the rigid side walls.

10. The container of claim 6 wherein at least one of the chambers is at least partially pre-evacuated.

11. A method of taking samples of blood or other fluid wherein the chambers of the container as in claim 6 are filled with samples by use of a hollow needle, and are separated fro subsequent analysis or test of the samples.

* * * * *